(12) United States Patent
Monica et al.

(10) Patent No.: US 6,773,909 B2
(45) Date of Patent: Aug. 10, 2004

(54) CONCENTRATION AND LYSIS OF ADENOVIRUS-INFECTED CELLS IN A SINGLE UNIT OPERATION

(75) Inventors: Thomas J. Monica, Walnut Creet, CA (US); Erik M. Whiteley, Richmond, CA (US)

(73) Assignee: Schering Aktiengesellschaft, Berlin (DE)

( * ) Notice: Subject to any disclaimer, the term of this patent is extended or adjusted under 35 U.S.C. 154(b) by 19 days.

(21) Appl. No.: 10/085,029

(22) Filed: Mar. 1, 2002

(65) Prior Publication Data

US 2003/0049829 A1 Mar. 13, 2003

Related U.S. Application Data

(60) Provisional application No. 60/272,034, filed on Mar. 1, 2001.

(51) Int. Cl.[7] .............................. C12N 7/00; C12N 7/02; A61K 39/23
(52) U.S. Cl. .................... 435/235.1; 435/239; 435/325; 424/233.1
(58) Field of Search ...................... 424/233.1; 435/239, 435/325, 235.1

(56) References Cited

U.S. PATENT DOCUMENTS 5,721,120 A    2/1998    Seifert et al.

OTHER PUBLICATIONS

G. Schoofs, et al. A high–yielding serum–free, suspension cell culture process to manufacture recombinant adenoviral vectors for gene therapy, Cytotechnology 28: 81–89, 1998.

R. Kempken et al., Assessment of a Disc Stack Centrifuge for Use in Mammalian Cell Separation, Biotechnology and Bioengineering, vol. 46, pp. 132–138 (1995).

R. Kempken et al., Clarification of animal cell cultures on a large scale by continuous centrifugation, Jounral of Industrial Microbiology, (1995) 14, 52–57.

Primary Examiner—James Housel
Assistant Examiner—Stacy B Chen
(74) Attorney, Agent, or Firm—Millen, White, Zelano & Branigan, P.C.

(57) ABSTRACT

A method is described to prepare intracellular biological entities (e.g. organisms, such as, e.g., viruses, particularly Adenoviruses; organelles, or biological molecules), comprising subjecting cells containing the biological entities to continuous centrifugation, under conditions effective to concentrate the cells into a cell pellet; and ejecting the pelleted cells from the centrifuge into a collection receptacle, under conditions effective to lyse cells; wherein no further steps effective to achieve cell lysis are performed.

26 Claims, 1 Drawing Sheet

CONCENTRATION AND LYSIS OF ADENOVIRUS-INFECTED CELLS IN A SINGLE UNIT OPERATION

This application claims priority of Provisional Application U.S. Ser. No. 60/272,034, filed Mar. 1, 2001.

FIELD OF THE INVENTION

This invention relates, e.g., to a method to prepare viruses (e.g., Adenoviruses) or other intracellular organisms.

DESCRIPTION OF THE INVENTION

This invention relates, e.g., to a method to release (prepare) intracellular biological entities (e.g., organisms, such as, e.g., viruses or virus particles, particularly Adenoviruses; organelles; or biological molecules), comprising subjecting cells which contain said biological entities to a continuous centrifugation procedure such that, following the concentration of the cells into a cell pellet and subsequent ejection from the centrifuge, the cells are sufficiently lysed to allow preparation of a high yield (per cell of the input material) of the biological entities. No additional steps effective to achieve cell lysis (e.g., a freeze-thaw step or microfluidization) are performed following ejection of the cell pellet from the centrifuge. In a preferred embodiment, organisms thus prepared retain a high degree of viability and/or infectivity; and entities such as organelles or biological molecules are substantially intact and/or biologically active.

One advantage of the method is that it allows one to concentrate and lyse cells in a single process step, thereby simplifying and reducing the cost of isolating intracellular (e.g., subcellular) biological entities from cells. Another advantage of the method is that a higher yield of biologically active intracellular material can be obtained than with other methods. Another advantage of the method is that it allows gentle lysis of the cells, such that intracellular biological entities, e.g., viruses, remain substantially intact and/or viable during the lysis procedure.

One embodiment of the invention is a method to prepare intracellular organisms from host cells containing said organisms, comprising subjecting the cells to continuous centrifugation under conditions effective to concentrate the cells into a cell pellet; and ejecting the pelleted cells from the centrifuge into a collection receptacle, under conditions effective to lyse cells; wherein no additional step effective to achieve cell lysis is performed. Another embodiment is a method to prepare intracellular organisms from host cells containing said organisms, comprising subjecting the cells to continuous centrifugation under conditions effective to concentrate the cells into a cell pellet; and ejecting the pelleted cells from the centrifuge into a collection receptacle, under conditions effective to lyse cells.

Another embodiment is a method as above, wherein the cells in the "ejectate" (the ejected cells) are substantially lysed and/or predominantly lysed; at least 50%, preferably at least 90%, of the cells are lysed; the cells are lysed as they are ejected; the intracellular organisms are viruses; the viruses are Adenoviruses; the Adenoviruses are recombinant Adenoviruses suitable for gene therapy; the yield/cell of Adenovirus particles or infectious Adenovirus is greater than that obtainable when cells containing said Adenovirus are lysed by a freeze-thaw procedure, e.g., the yield/cell of Adenovirus particles is about 1.2 to about 1.6 fold greater, or the yield/cell of infectious Adenovirus is about 1.5 to about 1.9 fold higher; the cells are animal cells, preferably mammalian or insect cells; the cells being ejected are under a relative centrifugal force of about 6,500 to 10,000 g, preferably about 7,000 to 9,000 g; said centrifugal force is about 7000 or 8,000 g; the pelleted cells are ejected through one or more ejection outlets having a rectangular shape and a cross-sectional area of about 50 to 500 mm$^2$; the cells are centrifuged in a Westfalia Centrifuge, Model CSA-1 or CSC-6; or the forces exerted on the cells at the time of ejection are effective to substantially lyse the cells.

Another embodiment is in a method of preparing intracellular viruses from cells containing said viruses by continuous centrifugation, the improvement comprising harvesting viruses from the ejected cell pellet directly, without performing an additional step effective to achieve cell lysis.

Another embodiment is a method to prepare a cell lysate, consisting of subjecting cells to continuous centrifugation to form a cell pellet; and ejecting said pelleted cells into a collection receptacle, wherein the collected cells are in the form of a cell lysate.

Another embodiment is a method to prepare a cell lysate, comprising subjecting cells to continuous centrifugation under conditions effective to concentrate the cells into a cell pellet; and ejecting the pelleted cells from the centrifuge into a collection receptacle, wherein the cells are in the form of a cell lysate; wherein no additional step effective to achieve cell lysis is performed.

Another embodiment is organisms (e.g., viruses, particularly Adenoviruses) prepared by any of the above methods.

Another embodiment is a method to prepare an organelle or biological molecule, comprising subjecting cells comprising said organelle or biological molecule to continuous centrifugation under conditions effective to concentrate the cells into a cell pellet; ejecting the pelleted cells from the centrifuge into a collection receptacle, wherein the cells in the "ejectate" (the ejected cells) are substantially lysed; wherein no additional step effective to achieve cell lysis is performed; and harvesting the organelle or biological molecule from the ejectate.

In the method of the invention, a culture of cells comprising a biological entity (e.g., an organism, organelle or biological material) of interest is fed through a continuous centrifuge. Typically, a concentrated "cell pellet" (which, of course, can comprise portions of cells or cell debris, in addition to intact cells) collects in a centrifuge container (e.g., a bowl), while spent medium is continuously released through a first outlet into a first collection receptacle. At predetermined time intervals, a feed of wash buffer (any suitable wash buffer, e.g., PBS freezing buffer) is optionally started in order to exchange any supernatant remaining in the centrifuge container with the wash buffer. Following this exchange (if employed), the wash buffer feed is discontinued and the concentrated cells are expelled from the centrifuge container through a second outlet into a second collection receptacle. Depending on the volume in which the cells are ejected, the cell concentration can be significantly greater than the initial concentration in the feed (e.g. about a 10-fold to 50-fold concentration typically about 30-fold).

Without wishing to be bound to any theory, it is proposed that the cells remain substantially intact as they are centrifuged into the cell pellet. That is, a small enough fraction of cells is lysed during centrifugation so that a significant quantity of intracellular organisms, organelles, or biological molecules is not prematurely released into the supernatant and shunted to the collection receptacle with the spent medium. Conditions of centrifugation can be routinely optimized for any cell of interest in order to minimize the amount of cell lysis during centrifugation. See, e.g., Examples 2 and 4 for typical centrifugation conditions.

It is also proposed that as the concentrated (pelleted) cells are then ejected from the centrifuge through an ejection outlet, they are subjected to forces (e.g., shear forces), such that the cells are substantially lysed. A variety of ejection means by which cells are ejected through an ejection outlet are encompassed by the invention. In general, cells are forced out of (expelled from) the centrifuge by centrifugal force through an ejection outlet when a barrier (e.g., a gate) is removed (e.g., lifted or displaced), at an opportune time, to expose the ejection outlet. Such barriers can be operated by any of a variety of mechanims, e.g., electronic (e.g., solenoid), pneumatic, magnetic or by a mechanical linkage. In a preferred embodiment, a gate is opened by a hydraulically operated drive, using water which does not contact the cells. Typically, the supernatant is continuously and separately discharged through a first outlet to a first collection receptacle, while the pellet is being discharged through a second outlet into a second collection receptacle. However, the supernatant and pellet fractions can, alternatively, be collected sequentially, through the same outlet.

By "substantially lysed" is meant herein, e.g., that a sufficient number of cells lyse to allow for high yields of biological entities (e.g., organisms, organelles, or biological molecules) in the ejectate. For example, greater than about 85%, 90% or 95% of the cells are lysed. Substantially lysed cells are sometimes referred to herein as a "lysate." Biological entities in the ejectate can be isolated (e.g., separated, purified) from undesired (e.g., contaminating) material in the ejectate without being subjected to further cell lysis procedures procedures which break open cells). Procedures to separate such biological entities from subcellular components, such as, e.g., cell membranes, are not considered cell lysis procedures and are permitted in the inventive method following the ejection step.

Cells subjected to the method of the invention can be "predominately" lysed, e.g. greater than about 50% of the cells are lysed, e.g., greater than 60%, 75%, 85%, 90% or 95% of the cells are lysed.

The forces to which cells are subjected during ejection from the centrifuge are a function of several factors, including, e.g., the g-forces exerted on the cells upon ejection, the pressure drop across the ejection outlet(s) (e.g., one or more bowl outlet ports), the shear force around the ejection outlet(s), and the impact force of the cells hitting the collection vessel (e.g., the outside chamber of the centrifuge). The g-force exerted on the cells during ejection is a function of both the radius of the centrifuge bowl and the revolutions per minute (rpm) at which it is spinning. Preferably, the cells are ejected under a relative centrifugal force of about 6,500 to 10,000 g, more preferably about 7,000 to 9,000 g, most preferably about 7000 or 8,000 g. The pressure drop across the ejection outlet and the shear force as cells pass through it are a function of many factors, including e.g., the dimensions of the outlet. In one embodiment, cells are ejected through a plurality of outlet ports, e.g., between about 2 to 20 outlet ports, preferably about 6 to 10; and each outlet port has a cross-sectional area of about 50 to 500 $mm^2$, preferably about 100–300 $mm_2$. The outlet ports can have any shape which provides forces (e.g., shear forces) sufficient to substantially lyse the cells; in a preferred embodiment, the outlet ports have a rectangular configuration.

Any continuous centrifuge, e.g., a disc stack or open bowl centrifuge, can be used in the method of the invention, provided that a high yield of intracellular biological entities (e.g., Adenoviruses) can be obtained following ejection of the cell pellet into a collection receptacle and harvesting of the biological entities from the ejectate. Among the desirable properties of such a centrifuge are that the cells are not subjected to significant forces (e.g., shear forces or centripetal forces) as they enter the container (bowl) or as they are spun into a cell pellet. In a preferred embodiment, the centrifuge has any of a variety of conventional low shear force inlet configurations. For example, it can utilize a hydrohermetic feed system (HHFS), in which the product stream/feed stream is accelerated by the product itself in the filled container. Suitable centrifuges include, e.g., the Westfalia continuous CSA-1 centrifuge with HHFS, which has a bowl capacity of 0.6L, a sediment holding volume of 0.25L, a maximum flow rate capacity of about 300L/h, a maximum speed of 10,000 rpm, and an adjustable back pressure of the waste medium; the Westfalia continuous CSC-6 centrifuge with HHFS, which has a bowl capacity of 1.8 L, a sediment holding volume of 0.7 L, a maximum flow rate capacity of about 300 L/h, a maximum speed of 12,000 rpm, and an adjustable back pressure of the waste medium; or the Alfa-Laval BTPX 205 continuous centrifuge, which has a capacity of 1200 L/h and a maximum bowl speed of 9650 rpm. The setting for back pressure of the waste medium can be optimized empirically. In a preferred embodiment, the back pressure is set at 20–30 psig, with a target of 25 psig for operation. One of skill in the art can readily design and/or optimize features of centrifuges so that they are functionally equivalent to the representative models discussed herein, e.g., with respect to cells remaining substantially intact during centrifugation, and cell lysis occurring during the ejection process.

Conditions of centrifugation and ejection, and the relevant parameters of the centrifuge used, can be optimized by conventional methods in order to achieve conditions which allow for substantial lysis of the cells, as well as minimal damage to the intracellular biological entities which are released during the lysis procedure. Among the centrifugation conditions which can be varied to optimize yields of the intracellular biological entities are, e.g., the centrifugation speed and the temperature during the centrifugation, as well as other parameters discussed elsewhere herein.

Any type of intracellular organism can be prepared using the method of the invention, provided that the organism is sufficiently robust to remain in a substantially intact and/or, preferably, viable and/or infectious form following the preparation procedure. By "substantially intact" is meant herein having sufficient physical structure to be useful for a given purpose. For example, an organism which loses some of its structural components during preparation, but which retains antigenic activity, can be used as a source for the preparation of, e.g., a vaccine. One advantage of the inventive method is that it allows for a higher yield of viable and/or infectious intracellular organisms per host cell than do other methods. The inventive method is particularly suitable for organisms which retain a high degree of viability and/or infectivity following the preparation procedure. Methods to measure viability and/or infectivity are routine and conventional. For Adenoviruses, for example, one can measure infectious particles with CPE, end point dilution, or a plaque forming assay, or can use FACS analysis, e.g., in conjunction with FITC labeled anti-penton (coat protein) antibody. See, e.g., Ayala et al. (2000), "A flow cytometry method for determining Adenoviral infectivity and for directly monitoring Adenovirus infections of suspension cultures," ACS National Meeting, March 2000, San Francisco. A "high" degree (yield) of viability or infectivity (e.g., per starting amount of host cells) is, of course, a relative term. It can be determined for each type of organism individually, taking into account the state of the art of purification of that particular organism. See, e.g., Example 4, which illustrates that infectious Adenovirus can be obtained in substantially higher yields per host cell (here, about a 1.5 to 1.9 fold increased recovery) when prepared by the method of the invention, than when prepared by other procedures.

Organisms prepared by the method of the invention can be pathogenic or non-pathogenic. Among the types of organisms which can be so prepared are any of a variety of parasites, e.g., protozoa, which can reside inside a host cell and which remain intact (and/or, preferably, viable and/or infectious) following preparation according to the method of the invention. Such organisms will be evident to one of skill in the art and include, e.g., malarial organisms (e.g., Plasmodium falciparum, malaria, vivax or ovale), Trypanosoma, Leishmania, Onchocerca, Schistosoma, Entomoeba, Cryptosporidia, Giardia, Trichomonas, Toxoplasma, or Pneumocyctis. In a preferred embodiment, viruses are prepared by the method of the invention. Any of a variety of such viruses can be prepared, including, e.g., DNA or RNA viruses, such as those falling into the following families: Parvoviruses, Adenoviruses, Herpesviruses, Poxviruses, Hepatitis B-like Viruses, Picomoviruses, Calciviruses, Astroviruses, Togaviruses, Flaviviruses, Coronoviruses, Paramyxoviruses, Rhabdoviruses, Filoviruses, Influenza viruses, Arenaviruses, Bunyaviruses, Reoviruses, Retroviruses and others which will be evident to one of skill in the art. Most preferred are Adenoviruses, e.g., avian or mammalian Adenoviruses, of any of the serotypes which have been identified. In a most preferred embodiment, recombinant viruses, such as, e.g., recombinant Adenoviruses or Adeno Associated Viruses which are suitable for gene therapy, are used. A variety of virus vectors have been described, including Adenoviruses and Adeno Associated Viruses defective in appropriate genes (e.g., E 1 gene deficient Adenovirus), which are suitable for gene therapy applications. Any of a variety of genes can serve as, e.g., markers or as therapeutic agents, and can be cloned into such vectors under the control of suitable regulatory sequences and then introduced into patients in methods of, e.g., gene therapy. The selection of suitable vectors and genes which can be expressed therein, and methods to make such constructs and to use them for in vitro or ex vivo methods of gene therapy, are conventional and well-known to those of skill in the art (see, e.g., *Sambrook, J et al* (1989). *Molecular Cloning: A Laboratory Manual*. Cold Spring Harbor Press, Cold Spring Harbor, N.Y.). Genes which can be used in the method of the invention include, e.g., genes encoding polypeptides such as enzymes, hormones, cytokines, growth factors, etc. Also, marker genes such as, e.g., lacZ or Green Fluorescent Protein can be expressed. Other types of organisms which can be prepared by the method of the invention include, e.g., infectious agents such as, e.g., prions. Of course, mutants or variant forms of any of the above organisms, including viruses, can be prepared by the method of the invention, as can recombinant, hybrid, chimeric, etc. forms of such organisms. Much of the discussion herein is directed to the preparation of Adenoviruses. However, one of skill in the art will recognize that any appropriate organism, organelle or biological molecule can be prepared by the methods described herein.

The intracellular organisms contained in a host cell can be introduced into that host by any of a variety of procedures. In one embodiment, the organisms infect the host cells and, as they grow and/or replicate, damage the host cells (e.g., lyse or otherwise kill them). In such a case, one of skill in the art can readily determine optimal conditions of infection, and optimal times at which to harvest the intracellular organism so as to maximize the yield. Example 3 illustrates typical conditions for infection of mammalian cells with Adenovirus. One need not use an intact organism to infect the host. For example, naturally occurring or recombinant nucleic acid, optionally in the presence of helper organisms or helper nucleic acid, can be introduced into a cell (e.g., transfected into it), using conventional, art-recognized methods. Appropriate packaging cells may also be used. In another embodiment, intracellular organisms are present in the host cells substantially throughout the cell cycle, e.g., they remain in a dormant, non-metabolizing, non-growing or non-replicating state, or they grow and/or replicate at a rate or in a manner which does not negatively affect the viability of the host cell.

The method is also useful for preparing cell lysates of cells which do not necessarily contain such organisms, and/or for preparing intracellular (e.g., subcellular) biological entities present in such lysates. By "biological entities" is meant herein, e.g., organisms, such as those described above; cellular organelles (e.g., mitochondria or chloroplasts), or organisms which reside within such organelles; or biological molecules (e.g., macromolecules such as, e.g., recombinant or non-recombinant proteins (e.g., cytokines or chemokines, receptors, or transcription factors), nucleic acids, etc., or smaller molecules such as, e.g., ligands, nucleosides, nucleotides, or oligonucleotides). The term "biological molecules" also encompasses macromolecular structures such as, e.g., receptors; complexes which comprise proteins, lipids, and/or nucleic acids; or the like. The lysis procedure of the inventive method can allow for more intact structures and/or increased biological activity of biological entities so obtained compared to those obtained using different lysis procedures. For example, protein complexes, complexes of nucleic acid and protein, receptor complexes, large DNA molecules, or chromatin molecules isolated by the method can remain more intact than when prepared by using other lysis procedures.

The intracellular biological entities can reside in any compartment of the host cell (e.g., the nucleus, the cytoplasm, a cellular organelle, or associated with an intracellular or cellular membrane), provided that, following ejection of the cells from the centrifuge, the intracellular biological entities can be recovered from the ejectate without being subjected to an additional step effective to achieve cellular lysis. As noted above, procedures to separate such biological entities from subcellular components, such as, e.g., cell membranes, are not considered cell lysis procedures and are permitted in the inventive method following the ejection step.

Many types of cells (e.g., host cells) can be used in the invention, and will be evident to one of skill in the art.

Preferably the cells are sufficiently robust to withstand forces encountered during the centrifugation process (e.g., centrifugal forces, shear forces), so that they do not lyse substantially before being ejected from the centrifuge, yet are sufficiently fragile to be lysed during the method (e.g., during the ejection step). Such cells include, e.g., animal cells, including insect cells, amphibian cells, mammalian cells (e.g., monkey, mouse or human cells such as, e.g., HEK-293 cells), and the like; one-celled organisms (e.g., bacteria, various types of yeast, etc.), particularly those which are, or which have been modified so as to be, sufficiently fragile to be lysed upon ejection; plant cells (e.g., Arabidopsis), particularly those which are or which have been modified so as to be sufficiently fragile to be lysed upon ejection; blood cells; or mutants or variants of any such cells. A preferred type of host cell is one which supports the replication of Adenoviruses, e.g. defective Adenoviruses, allowing them to reach high titers. For example, in one embodiment, packaging cell lines which contain a helper gene such as, e.g., an Adenovirus E1 gene, e.g., one from Adeno type 5, can be used.

Of course, it is not required that the cell remain intact during the centrifugation procedure. For example, a biological entity of interest can remain attached to or otherwise associated with a subcellular portion of a non-intact cell (e.g., with a cellular organelle, a fraction of cell membrane, a piece of cell debris, or the like) which forms part of the "cell pellet" upon centrifugation, and can be recovered followed ejection of that material from the centrifuge into a collection receptacle.

Additional steps, all of which are conventional, can be employed before or after the inventive method of preparing intracellular biological entities.

For example, cultures of cells to be centrifuged can be prepared by a variety of procedures, in small quantities or in large amounts (e.g., in large volume fermentor reactors). Conditions for infecting cells, propagating them (e.g., selecting appropriate culture media, and monitoring conditions such as cell density, pH, oxygen utilization, temperature, etc.) and harvesting them (e.g., choosing optimum times after infection to harvest the cells) are conventional and readily optimized. For conditions for growing Adenoviruses, see, e.g., Schoofs et al. (1998). "A high-yielding serum-free, suspension cell culture process to manufacture recombinant adenoviral vectors for gene therapy," Cytotechnology 28, 81–89 and Monica et al. (2000). "Monitoring Adenovirus infections with on-line and off-line methods, *Biotechnology Progress* 16, 866–871."

The cells are introduced into the centrifuge at a feed flow rate which is selected so as to optimize the yield of biological entities therein. That is, the rate is slow enough to permit efficient pelleting of the cells (to minimize loss of cells in the supernatant stream), yet fast enough to provide efficient throughput. For example, in a typical procedure using a CSA-1 Westfalia Centrifuge, the feed rate is about 1–3 L/min, and the bowl speed is about 6–12,000 rpm, preferably 10,000 rpm.

Following ejection of cells from the centrifuge into a collection receptacle, the cells or cell lysates are "harvested." Harvesting cells can mean merely collecting the crude lysate of cells in the collection receptacle, or, optionally, performing further steps to isolate (e.g., purify, separate) the biological entities from undesirable contaminants, such cellular components, in the ejectate. Among the conventional procedures for purifying Adenoviruses are, for example, centrifugation or expanded bed adsorption chromatography to remove cell debris and/or to concentrate the virus, size exclusion chromatography, ion exhange (e.g., DEAE) chromatography, ultracentrifugation, ultrafiltration, etc.

Expanded Bed Adsorption chromatography (a.k.a. Fluidized Bed) is a technique used in protein and viral purification. This technique is based on the fluidization of chromatographic resins to a minimum expansion of two fold of the settled bed height. By expanding the resin bed, this technique combines several unit operations with one step. Expanded Bed Adsorption (EBA) chromatography eliminates the need for a centrifugation step to remove cellular debris that is present in raw harvests. In addition, the use of chromatographic resins for this step provides an initial purification and concentration step for any process.

In order to achieve the degree of bed expansion, fluid flows from the bottom of the column to the top of the column at a constant linear velocity. Once the crude lysate is loading onto the column and all the cellular debris are are cleared, the column is packed with a downward flow as used in conventional chromatographic techniques. The target protein or viral product is eluted using standard chromatographic methods.

The starting material for the EBA is crude harvest derived from a continuous centrifuge (e.g., a Westphailia centrifuge), Mircofluidized, or Freeze-Thawed. The harvest is loaded directly onto the column with either Fractogel TMAE or Streamline QXL resin in expanded mode. The column is equilibrated with equilibration buffer prior to loading and the degree of expansion is maintained throughout the process until the column has reached a stable UV baseline after loading. Upon completion of column loading, the flow is reversed and the column is packed hydraulically with a downward flow. After the column is packed properly, the resin bed is washed with 5 column volume (CV) of equilibration before starting the elution gradient. The eluate is collected and analyzed by AIEX-HPLC, RP-HPLC, Pico Green, QIA, and slot blot. Other assays not listed may also be performed.

The eluate pool is optionally further processed either by Size Exclusion Chromatography (SEC) or by ultrafiltration. In the case of ultrafiltration, the column eluate is diluted 1:100 with buffer and the volume is reduced to approximately 300 mL (including system flushes). The collected concentrate is formulated with 2% sucrose and frozen at –70C. Once again, samples are taken for various analysis to ensure product quality and purity.

If SEC is used, an appropriately sized SEC column is packed with Tosohaas HW-65F resin and the column is loaded with 10% column volume of the eluate from the EBA step. The virus elutes in the excluded volume and fractions are collected and pooled according to the UV trace. The elution is pooled and formulated with 2% sucrose. The formulated pool is frozen at –70C. until it is thawed for vialing. Samples of the pooled material are taken for various analysis to ensure product quality and purity.

EXAMPLES

Figure 1:
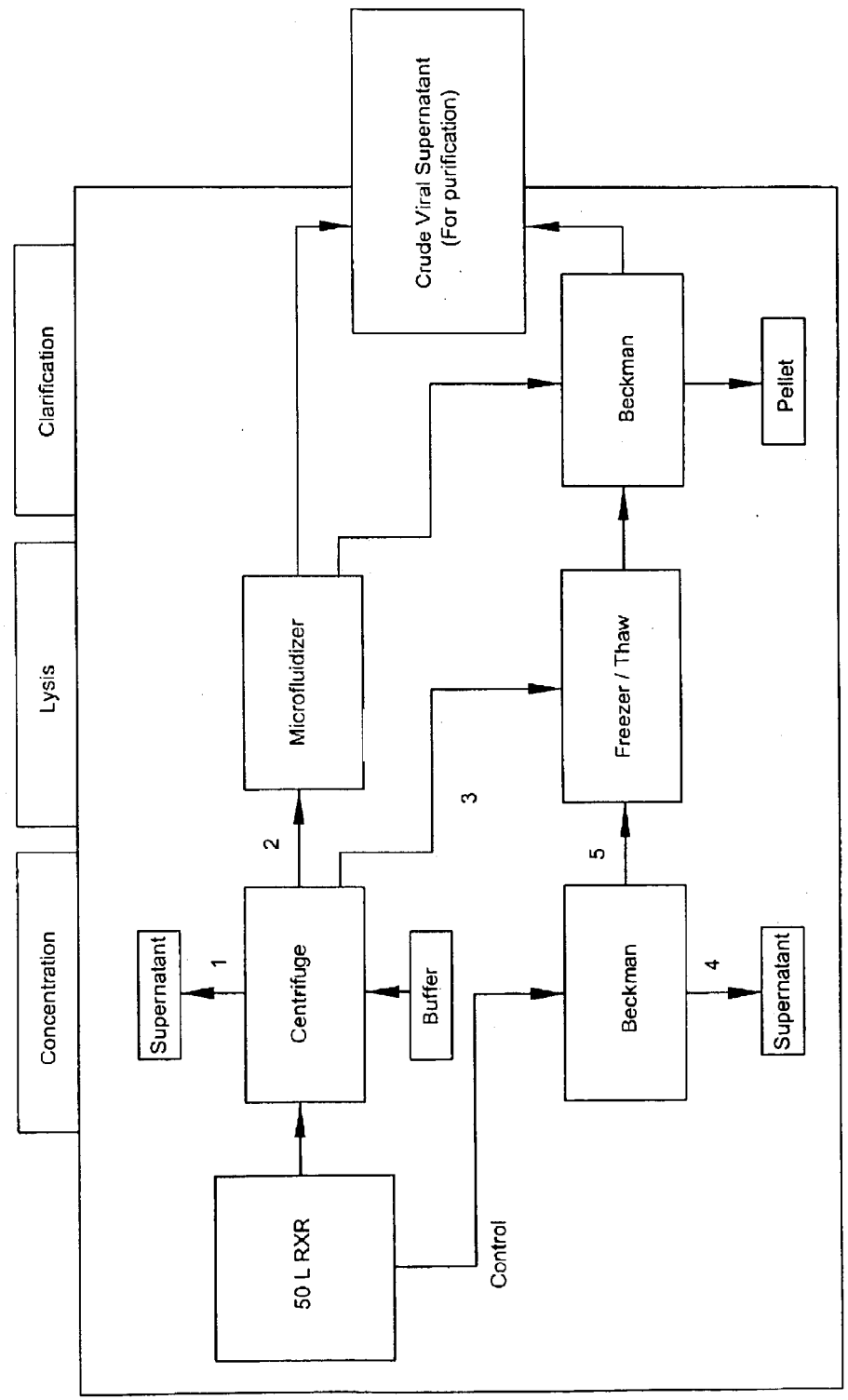
FIG. 1 is a schematic illustration of a test procedure using a continuous centrifuge.

Example 1 —Test procedures using a continuous centrifuge (See FIG. 1)

A cell culture (infected or non-infected) is fed into the centrifuge bowl of a continuous centrifuge (e.g., a Westfalia CSA-1 continuous centrifuge) for a predetermined time interval, during which the medium is continuously discharged (step 1 in FIG. 1). At the conclusion of this interval, the cell culture feed is stopped and a buffer solution is fed into the bowl through a second flush line for an exchange of medium for a buffer (e.g., a freezing buffer). After the flush is stopped, the contents of the bowl (concentrated cell pellet in buffer) are then hydraulically ejected from the centrifuge by isolated operating water. The feed of the cell culture is then restarted and the process continued until the harvest is complete.

In test procedures, portions of the concentrated cell culture are then subjected to an additional lysis step, in order to determine, e.g., if an additional lysis procedure results in further lysis of the cells in the ejectate. In one set of experiments (step 2 in FIG. 1), the ejectate is subjected to treatment in a Microfluidics HC-2000 Microfluidizer, which uses pneumatic intensifier pumps to supply a desired pressure at a constant rate to the product stream. The pump drives the product through fixed geometry microchannels inside an interaction chamber. As a result, the product stream, e.g., mammalian cells, accelerates to high velocities, creating shear rates within the product stream producing high yield cell disruption. Following treatment in the Microfluidizer, the sample can be clarified by low speed centrifugation, and the supernatant examined for the presence of intracellular biological entities. In another set of experiments (step 3 in FIG. 1), the ejectate is subjected to a freeze-thaw procedure, in which the ejectate is subjected to three alternating cycles of freezing and thawing. Following the freeze-thaw procedure, the sample can be clarified by low speed centrifugation, and the supernatant examined for the presence of intracellular biological entities. In the description herein of assays of samples from the above steps, e.g., in Tables 1–4 of Example 4, the samples from the various steps are referred to as follows: the media which is continuously discharged is "Discarded Growth Medium"; the ejectate from the centrifuge is "Ejectate —Concentrated Cell pellet"; a portion of the ejectate which is subjected to the freeze-thaw procedure and clarified by low speed centrifugation is "Freeze-Thaw —Final Processed Supernatant"; and a portion of the ejectate which is subjected to treatment with a Microfluidizer and clarified by low speed centrifugation is "Microfluidizer —Final Processed Supernatant."

For comparison, a portion of the cell culture is processed, not in a continuous centrifuge, but by a "control" process (step 5 in FIG. 1). The cells are subjected to batch centrifugation to concentrate the cell pellet from the conditioned media, and the supernatant is removed and replaced with a smaller volume of a buffer (e.g., a freezing buffer), typically in a volume to achieve about a 30X reduction in volume. The cells are resuspended and subjected to three alternating cycles of freezing and thawing. In the description herein of assays of samples from the above steps, e.g., in Tables 1–4 of Example 4, the samples from the various steps are referred to as follows: the supernatant (following concentration) is "Discarded Growth Medium"; and the resuspended pellet which is subjected to the freeze-thaw procedure and clarified by low speed centrifugation is "Freeze-Thaw —Final Processed Supernatant."

Samples are analyzed using AIEX-HPLC analytical chromatography for total particle counts; Trypan Blue Staining for visual inspection; and the Coulter Multisizer for mean particle size. Final crude (unpurified) viral supernatants from the centrifuge, Microfluidizer and Control Streams are also analyzed using the Quick Infectivity Assay (QIA) to determine infectious titers. The QIA is a colorimetric assay based on conventional cytotoxic effect assays for calculation of the infectious viral titers.

Example 2—Testing a Westfalia Continuous Centrifuge with Uninfected Cells

The Westfalia CSA-1 Continuous Centrifuge is tested with uninfected mammalian cells grown in cell culture medium +1% serum in a 50 L reactor. The reactor working volume is 43 L. Cells are grown to a density of $1 \times 10^6$ cells/mL with greater than 90% viability. For this and all other experiments described in these examples, the feed rate to the Westfalia is held at 1.5 L/min and the bowl is run at approximately 9000 rpm.

To determine if lysis occurs within the concentrated cell stream, but not within the feed stream, the concentration of lactate dehydrogenase (LDH), a stable cytosolic enzyme released upon cell lysis, is measured in all streams using the colorimetric CytoTox 96 Non-radioactive Assay (Promega Corporation).

A LDH positive control is used to construct a standard concentration curve in a 96-well plate. A minimum LDH concentration sample representing the control centrifugation is prepared by spinning a culture sample for 15 minutes at 1000 rpm and using the culture supernatant as the basal LDH concentration. The lysed cell LDH concentration sample is created through 3 freeze-thaw cycles of cell culture followed by a 15 minute spin at 1000 rpm representing the maximum LDH concentration from within the media.

Visual hemocytometer counts and particle size distributions are used to analyze samples from the initial feed stream, the concentrated cell stream (the "ejectate"), and the waste supernatant stream. Particle size distributions reflect, e.g., the accumulation of cell debris as well as whole cells and are therefore an indication of cell lysis.

Samples for the LDH Assay are taken from the supernatant stream at 5-minute intervals during the 20 minute separation.

| Cell Staining and Coulter Counter Results | |
|---|---|
| Cell Culture: | 0.84 × 10⁶ cells/mL 94% viability |
| Westfalia supernatant outlet: | no viable cells, large debris |
| Westfalia concentrated cell pellet (~2.4 L) | some viable cells, most cells appear lysed |

Along with the appearance of more cell debris during staining, Coulter counter measurements demonstrate a reduction in particle size during processing. This demonstrates that the cells in the ejectate are substantially lysed.

The average LDH concentration for the supernatant outlet stream from the Westfalia is only 3.3% higher than the back ground value from the cell culture control supernatant. Ejection of the cell pellet from the bowl lyses the cell fraction but it appears that no additional lysis occurs when the cells are entering the centrifuge chamber.

If desired, biological entities present in the ejectate (e.g., organelles or biological molecules as defined herein) can be further isolated (e.g., subjected to purification steps).

Example 3—Preparation of Infected Cells

In general, mammalian cells, grown in cell culture medium, are infected at a cell density between about $0.5 \times 10^6$ cells/mL and about $1 \times 10^6$ cells/mL with Adenovirus containing either a therapeutic transgene or a marker(e.g., lacZ) transgene, at a multiplicity of infection between about 15 and 50 infectious particles/cell. The cultures are harvested approximately 48 hours post-infection.

Example 4—Testing a Westfalia Continuous Centrifuge with Infected Cells

The Westfalia Continous Centrifuge is utilized to process four additional reactor preparations of Adenovirus infected cells.

Experiment #1

Cells which can serve as packaging cell lines are grown in cell culture medium +2% serum. The cells are infected with recombinant Adenovirus containing a transgene in a 42 L working volume. At the time of harvest the cell density is $0.56 \times 10^6$ cells/mL with 66.1% viability.

Samples from the various steps are examined using cell staining, Coulter counter particle size distribution, AIEX-HPLC chromatography, and infectivity assays.

The reduction in volume for the control process is 28X while processing with the Westfalia results in a volume reduction of approximately 18X.

| Visual examination using staining: | |
|---|---|
| Cell culture: | $0.56 \times 10^6$ cells/mL with 66.1% viability |
| Control supernatant: | no visible cells, some small debris |
| Control concentrated pellet: | $12.5 \times 10^6$ cells/mL ~74% viability, little debris |
| Control lysed pellet: | no viable cells, large cells clumps, difficult to count |
| Westfalia supernatant outlet: | supernatant is clear of debris and viable cells |
| Westfalia concentrated cell pellet: | $\sim 4 \times 10^6$ cells/mL 25% viability in 1.8 L, significant disruption of cells, lots of debris |
| Microfluidizer lysed cell outlet: | $0.17 \times 10^6$ cells/mL 5.9% viability, mostly uniform small-sized debris |

The Coulter counter is used to obtain mean particle size comparisons between the control and scale-up processes at each unit operation.

Virus Recovery

Total virus particles are determined using anion exchange chromatography, and infectious particle concentrations are calculated using the QIA. (See Table 1). Samples are analyzed from the Control Process (Discarded Growth Medium; Final Processed Supernatant) and from the Westfalia Centrifuge Process (Discarded Growth Medium; ejectate following the freeze-thaw procedure; and ejectate following treatment with the Microfluidizer), and the results of the assays are shown in Table 1. For a summary of each of these steps, and of the terms in the table, see Example 1.

TABLE 1

Total and infectious virus titers from Experiment #1

| | | Total Virus/cell | % Difference from Control | IU/cell | % IU |
|---|---|---|---|---|---|
| CONTROL PROCESS | | | | | |
| | Discarded Growth Medium | Not Detected | — | Not Tested | — |
| Freeze-Thaw | Final Processed Supernatant | $3.8 \times 10^4$ | 0.0 | $1.1 \times 10^3$ | 3.0 |
| WESTFALIA | | | | | |
| | Discarded Growth Medium | Not Detected | — | Not Tested | — |
| Freeze-Thaw | Final Processed Supernatant | $5.2 \times 10^4$ | 37.0 | $2.2 \times 10^3$ | 4.3 |
| Microfluidizer | Final Processed Supernatant | $4.9 \times 10^4$ | 29.0 | $2.1 \times 10^3$ | 5.7 |

Experiment #2

Cells as in Experiment #1 are grown in cell culture medium +5% serum. The cells are infected with recombinant Adenovirus containing a marker gene, in cell culture medium +2% serum (42 L working volume). At the time of harvest the cell density is $1.46 \times 10^6$ cells/mL with 75% viability.

The reduction in volume for the control process is 28X while processing with the Westfalia results in a volume reduction of approximately 23X.

| Visual examination using staining | |
|---|---|
| Cell culture: | $1.46 \times 10^6$ cells/mL with 75% viability |
| Control supernatant: | some visible cells |

-continued

| Visual examination using staining | |
|---|---|
| Control concentrated pellet: | 23.2 × 10⁶ cells/mL 72.4% viability |
| Control lysed pellet: | 14.4 × 10⁶ cells/mL, no viable cells, large cell aggregates |
| Westfalia supernatant outlet: | supernatant is clear of debris and viable cells |
| Westfalia concentrated cell pellet: | 3.2 × 10⁶ cells/mL 0% viability in 1.8 L, significant disruption of cells, lots of debris |
| Microfluidizer lysed cell outlet: | no whole cells, uniform distribution of debris |

The Coulter counter is used to obtain mean particle size comparisons between the control and scale-up processes at each unit operation.

Virus Recovery

Total virus particles are determined using anion exchange chromatography and infectious particle concentrations are calculated using the QIA (Table 2). Samples are tested as in the previous experiment with the addition of sampling of the concentrated cell pellet stream from the Westfalia prior to further processing ("Concentrated Cell Pellet").

TABLE 2

Total and infectious virus titers from Experiment #2

| | | Total Virus/Cell | % Difference from Control | IU/cell | % IU |
|---|---|---|---|---|---|
| CONTROL | | | | | |
| | Discarded Growth Medium | 9.8 × 10² | −97.0 | Not Tested | — |
| | Final Processed Supernatant | 3.2 × 10⁴ | 0.0 | 6.2 × 10² | 1.9 |
| WESTFALIA | | | | | |
| | Discarded Growth Medium | 9.4 × 10² | −97.0 | Not Tested | — |
| Ejectate | Concentrated Cell pellet | 5.3 × 10⁴ | 68.0 | ~1.2 × 10³ | 2.0 |
| Freeze-Thaw | Final Processed Supernatant | 5.9 × 10⁴ | 85.0 | 1.2 × 10³ | 2.0 |
| Microfluidizer | Final Processed Supernatant | 5.2 × 10⁴ | 62.0 | 8.2 × 10² | 1.6 |

Experiment #3

Cells as in Experiment #1 are grown under perfusion in a 10 L seed reactor in serum-free cell culture medium, transferred and infected in 48 L working volume. The cells are infected with recombinant Adenovirus containing a marker gene. At the time of harvest the cell density is $0.64 \times 10^6$ cells/mL with 80.4% viability.

The reduction in volume for the control process is 20X while processing with the Westfalia results in a volume reduction of approximately 26X.

| Visual examination using staining | |
|---|---|
| Cell culture: | 0.64 × 10⁶ cells/mL with 75% viability |
| Control supernatant: | 0.01 × 10⁶ cells/mL, small bits of debris |
| Control concentrated pellet: | 12 × 10⁶ cells/mL 72.4% viability |
| Control lysed pellet: | 6.5 × 10⁶ cells/mL, no viable cells |
| Westfalia supernatant outlet: | supernatant is clear of debris and cells |
| Westfalia concentrated cell pellet: | no whole cells, lots of debris of various sizes, 1.8 L volume |
| Microfluidizer lysed cell outlet: | no whole cells, uniform distribution of debris |

The Coulter counter is used to obtain mean particle size comparisons between the control and scale-up processes at each unit operation.

Virus recovery

Total virus particles are determined using anion exchange chromatography and infectious particle concentrations are calculated using the QIA (Table 3).

TABLE 3

Total and infectious virus titers from Experiment #3

| | | Total Virus/Cell | % Difference from Control | IU/cell | % IU |
|---|---|---|---|---|---|
| CONTROL | | | | | |
| | Discarded Growth Medium | 4.9 × 10⁴ | −85.0 | Not Tested | — |
| | Final Processed Supernatant | 3.1 × 10⁵ | 0.0 | 1.4 × 10⁴ | 4.2 |

TABLE 3-continued

Total and infectious virus titers from Experiment #3

| | | Total Virus/Cell | % Difference from Control | IU/cell | % IU |
|---|---|---|---|---|---|
| WESTFALIA | | | | | |
| | Discarded Growth Medium | $5.4 \times 10^4$ | −84.0 | Not Tested | — |
| Ejectate | Concentrated Cell Pellet | $2.9 \times 10^5$ | −12.0 | $2.4 \times 10^4$ | 13.4 |
| Freeze-Thawed | Final Processed Supernatant | $4.1 \times 10^5$ | 22.0 | $1.6 \times 10^4$ | 4.2 |
| Microfluidizer | Final Processed Supernatant | $2.7 \times 10^5$ | −19.0 | $1.5 \times 10^4$ | 6.1 |

Experiment #4

Cells as in Experiment #1 are grown under perfusion in a 10 L seed reactor in serum-free cell culture medium, transferred and infected in a 45 L working volume. The cells are infected with a recombinant Adenovirus containing a transgene. At the time of harvest the cell density is $0.45 \times 10^6$ cells/mL with 74.2% viability.

The reduction in volume for the control process is 20X while processing with the Westfalia results in a volume reduction of approximately 24X.

| Visual examination using staining | |
|---|---|
| Cell culture: | $0.45 \times 10^6$ cells/mL with 74.2% viability |
| Control supernatant: | $0.04 \times 10^6$ cells/mL, not much debris |
| Control concentrated pellet: | $8.4 \times 10^6$ cells/mL 73.4% viability |
| Control lysed pellet: | no viable cells; large debris and cell aggregates |
| Westfalia supernatant outlet: | supernatant is clear of debris and cells |
| Westfalia concentrated cell pellet: | no cells, small size debris; some larger debris in 1.8 L |
| Microfluidizer lysed cell outlet: | uniform debris |

The Coulter counter is used to obtain mean particle size comparisons between the control and scale-up processes at each unit operation.

Virus recovery

Total virus particles are determined using anion exchange chromatography and infectious particle concentrations are calculated using the QIA (Table 4).

TABLE 4

Total and infectious virus titers from Experiment #4

| | | Total Virus/Cell | % Difference from Control | IU/cell | % IU |
|---|---|---|---|---|---|
| CONTROL | | | | | |
| | Discarded Growth Medium | Not Detected | — | Not Tested | — |
| | Final Processed Supernatant | $2.4 \times 10^5$ | 0.0 | $5.6 \times 10^3$ | 2.3 |
| WESTFALIA | | | | | |
| | Discarded Growth Medium | Not Detected | — | Not Tested | — |
| Ejectate | Concentrated Cell Pellet | $3.0 \times 10^5$ | −25.2 | $8.5 \times 10^3$ | 2.8 |
| Freeze-Thawed | Final Processed Supernatant | $3.1 \times 10^5$ | 31.0 | $7.4 \times 10^3$ | 2.4 |
| Microfluidizer | Final Processed Supernatant | $2.2 \times 10^5$ | −10.1 | $9.3 \times 10^3$ | 4.3 |

Examining total and infectious virus counts shows that the virus concentrations directly from the Westfalia meet or exceed the concentrations from other procedures. Results from the harvest experiments also reveal an invaluable advantage of using this harvest process. Upon ejection of the cell pellet from the unit, the cells are significantly lysed, yet the lysis occurs substantially entirely in the product stream, segregated from any waste streams. Total and infectious virus numbers demonstrate that the Adenovirus concentration is not harmed during this lysis. Further analysis of the mean particle sizes of the freeze-thaw procedure ("Control Procedure") compared to the Westfalia/Microfluidizer procedure, shows that not only does the Westfalia processing lyse the cells, but it appears more effective than the freeze-thaw (control) procedure. During the 3 cycles of freeze-thaw (control process), the cells appear to lyse; however, analysis of particle size indicates that the degree of lysis is less than that obtained with the Westfalia procedure. This is confirmed by visual observations. There is also relatively little mean diameter reduction from further processing of the Westfalia material with the microfluidizer in the scale-up process. The yield per cell of virus particles or infectious units does not increase if ejectates taken directly from the Westafalia are subjected to further "lysis" procedures, such as three cycles of freeze-thaw or treatment with a microfluidizer, nor does the degree of cell lysis increase.

As can be seen from the Tables, the yield/cell of Adenovirus particles is in a range of about 1.2 to about 1.6 fold greater when obtained by centrifugation and ejectation in the Westfalia than when obtained by batch centrifugation followed by three cycles of freeze-thaw. The yield of infectious Adenovirus is in a range of about 1.5 to about 1.9 fold higher. In other combinations of Adenovirus and cells, the increase in yield/cell can be higher. The yields can be determined with conventional methods, e.g., as described elsewhere herein.

From the foregoing description, one skilled in the art can easily ascertain the essential characteristics of this invention, and without departing from the spirit and scope thereof, can make changes and modifications of the invention to adapt it to various usage and conditions.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The entire disclosure of all applications, patents and publications cited above are hereby incorporated by reference.

What is claimed is:

1. A method to release viruses from animal cells containing said viruses, comprising
   subjecting the cells to continuous centrifugation under conditions effective to concentrate the cells into a cell pellet, and
   ejecting the pelleted cells from the centrifuge through one or more ejection outlets into a collection receptacle, under conditions effective to lyse said cells solely by exertion of forces generated by said centrifugation and to release said viruses from said cells.

2. The method of claim 1, wherein greater than about 85% of the cells are lysed.

3. The method of claim 1, wherein greater than 50% of the cells are lysed.

4. The method of claim 1, wherein the cells are lysed as they are ejected.

5. The method of claim 1, wherein the viruses are Adenoviruses.

6. The method of claim 5, wherein the Adenoviruses are recombinant Adenoviruses suitable for gene therapy.

7. The method of claim 5, wherein the yield/cell of Adenovirus particles or infectious Adenovirus is greater than that obtainable when cells containing said Adenovirus are lysed by a freeze-thaw procedure.

8. The method of claim 7, wherein the yield/cell of Adenovirus particles is about 1.2 to about 1.6 fold greater than that obtainable when cells containing said Adenovirus are lysed by a freeze-thaw procedure.

9. The method of claim 7, wherein the yield/cell of infectious Adenovirus is about 1.5 to about 1.9 fold greater than that obtainable when cells containing said Adenovirus are lysed by a freeze-thaw procedure.

10. The method of claim 1, wherein the cells are mammalian or insect cells.

11. The method of claim 1, wherein the cells being ejected are under a relative centrifugal force of 6500 to 7500 g.

12. The method of claim 11, wherein said centrifugal force is about 7000 g.

13. The method of claim 1, wherein the pelleted cells are ejected through one or more ejection outlets having a rectangular shape and a cross-sectional area of 50 to 500 mm$^2$.

14. The method of claim 11, further wherein the pelleted cells are ejected through one or more ejection outlets having a rectangular shape and a cross-sectional area of 50 to 500 mm$^2$.

15. The method of claim 1, wherein the cells are centrifuged in a Westfalia Centrifuge, Model CSA-1 or CSC-6.

16. The method of claim 1, wherein the forces exerted on the cells at the time of ejection are effective to lyse greater than about 85% of the cells.

17. In a method of releasing intracellular viruses from cells containing said viruses by continuous centrifugation, the improvement comprising harvesting viruses directly from a cell pellet farmed by said centrifugation by ejecting said pelleted cells through one or more ejection outlets, under conditions effective to lyse said cells solely by exertion of forces generated by said centrifugation.

18. A method to prepare a cell lysate, consisting of subjecting cells to continuous centrifugation to form a cell pellet, and ejecting said pelleted cells through one or more ejection outlets into a collection receptacle under conditions effective to lyse said cells solely by exertion of forces generated by said centrifugation and to form a cell lysate.

19. A method to prepare a cell lysate, comprising
    subjecting cells to continuous centrifugation under conditions effective to concentrate the cells into a cell pellet, and
    ejecting the pelleted cells from the centrifuge through one or more ejection outlets into a collection receptacle under conditions effective to lyse said cells solely by exertion of forces generated by said centrifugation and to form a cell lysate.

20. A method to release viruses from animal cells
    containing said viruses, comprising
    subjecting the cells to continuous centrifugation under conditions effective to concentrate the cells into a cell pellet, and
    ejecting the pelleted cells from the centrifuge through one or more ejection outlets into a collection receptacle, under conditions effective to lyse said cells solely by exertion of forces generated by said centrifugation and to release said virus from said cells.

21. The method of claim 20, wherein greater than about 85% of the cells are lysed.

22. A method to release viruses from animal cells containing said viruses, consisting essentially of
    subjecting the cells to continuous centrifugation under conditions effective to concentrate the cells into a cell pellet, and
    ejecting the pelleted cells from the centrifuge through one or more ejection outlets into a collection receptacle, under conditions effective to lyse said cells solely by exertion of forces generated by said centrifugation and release said viruses from said cells.

23. A method to release an intracellular organism, or an intracellular organelle or biological molecule, from host cells containing said organism, organelle or biological molecule, comprising subjecting the cells to continuous centrifugation under conditions effective to concentrate the cells into a cell pellet, and ejecting the pelleted cells from the centrifuge through one or more ejection outlets into a collection receptacle, under conditions effective to lyse said cells solely by exertion of forces generated by said centrifugation and to release said organism, intracellular organelle or biological molecule from said cells.

24. The method of claim 1, further comprising subjecting the ejected cells to expanded bed chromatography.

25. The method of claim 1, wherein the forces exerted on the cells at the time of ejection are effective to lyse greater than about 50% of the cells.

26. The method of claim 20, wherein greater than about 50% of the cells are lysed.

* * * * *

UNITED STATES PATENT AND TRADEMARK OFFICE
CERTIFICATE OF CORRECTION

PATENT NO.     : 6,773,909 B2
DATED          : August 10, 2004
INVENTOR(S)    : Thomas J. Monica et al.

It is certified that error appears in the above-identified patent and that said Letters Patent is hereby corrected as shown below:

Title page,
Item [75], Inventor, "Walnut Creet" should read -- Walnut Creek --.

Column 18,
Line 24, "cell pellet farmed" should read -- cell pellet formed --.
Line 54, "said virus" should read -- said viruses --.

Signed and Sealed this

Twenty-fourth Day of May, 2005

JON W. DUDAS
*Director of the United States Patent and Trademark Office*